United States Patent
Jaworski et al.

(10) Patent No.: US 7,499,377 B2
(45) Date of Patent: Mar. 3, 2009

(54) PRESSURE WAVE PIEZOELECTRIC SENSOR

(75) Inventors: Artur J Jaworski, Stockport (GB); Jack Hale, Gateshead (GB); Thomas Dyakowski, Sale (GB); Neil White, Southampton (GB)

(73) Assignees: The University of Manchester, Manchester (GB); The University of Southampton, Southampton (GB); The University of Newcastle, Newcastle Upon Tyne (GB)

( * ) Notice: Subject to any disclaimer, the term of this patent is extended or adjusted under 35 U.S.C. 154(b) by 233 days.

(21) Appl. No.: 10/569,899

(22) PCT Filed: Aug. 27, 2004

(86) PCT No.: PCT/GB2004/003805

§ 371 (c)(1),
(2), (4) Date: Feb. 28, 2006

(87) PCT Pub. No.: WO2005/022106

PCT Pub. Date: Mar. 10, 2005

(65) Prior Publication Data

US 2007/0007861 A1 Jan. 11, 2007

(30) Foreign Application Priority Data

Aug. 28, 2003 (GB) ................... 0320168.8

(51) Int. Cl.
*G01L 9/08* (2006.01)
(52) U.S. Cl. ..................................... 367/157
(58) Field of Classification Search ............ 310/21, 310/311, 314, 323, 332, 338; 367/20, 155, 367/160, 180, 171, 157; 381/174; 29/504, 29/594
See application file for complete search history.

(56) References Cited

U.S. PATENT DOCUMENTS 2,963,641 A * 12/1960 Nanz ........................... 324/376
2,963,642 A * 12/1960 Arbogast et al. ............. 324/376
3,832,762 A * 9/1974 Johnston et al. ............. 29/25.35

(Continued)

FOREIGN PATENT DOCUMENTS

EP 1660854 A1 * 5/2006

(Continued)

OTHER PUBLICATIONS

Chen, Xiang-Dong, et al., "0-3 Piezoelectric composite film with high d33 coefficient" in Sensors and Actuators A 65, Sep. 18, 1998, pp. 194-196.*

(Continued)

*Primary Examiner*—Dan Pihulic
(74) *Attorney, Agent, or Firm*—Pillsbury Winthrop Shaw Pittman LLP

(57) ABSTRACT

A sensing device and method. The device includes a first element and a second element. Each of the elements includes a first electrode, and a second electrode, and a piezoelectric layer between and connected to the first and second electrode. The first electrode, second electrode and piezoelectric layer of each element form a pressure wave transducer. The first and second elements are oriented such that the second electrode of the first element faces the second electrode of the second element. The elements are displaced from one another such that the second electrodes form the plates of a capacitor.

4 Claims, 4 Drawing Sheets

U.S. PATENT DOCUMENTS

| | | | | |
|---|---|---|---|---|
| 4,011,748 A | * | 3/1977 | Bond et al. | 73/601 |
| 4,398,539 A | * | 8/1983 | Proudian | 600/447 |
| 4,954,811 A | | 9/1990 | Chatigny et al. | 340/550 |
| 4,984,222 A | | 1/1991 | Beauducel et al. | 367/159 |
| 5,251,627 A | * | 10/1993 | Morris | 600/398 |
| 5,548,564 A | * | 8/1996 | Smith | 367/140 |
| 6,286,360 B1 | * | 9/2001 | Drzewiecki | 73/24.01 |
| 2007/0007861 A1 | * | 1/2007 | Jaworski et al. | 310/338 |

FOREIGN PATENT DOCUMENTS

| | | |
|---|---|---|
| GB | 1 354 865 | 6/1974 |
| WO | WO 99/06891 | 11/1999 |
| WO | WO 2005022106 A1 * | 3/2005 |

OTHER PUBLICATIONS

International Search Report date Dec. 17, 2004, for PCT Application PCT/GB2004/003805.

* cited by examiner

PRESSURE WAVE PIEZOELECTRIC SENSOR

RELATED APPLICATIONS

This application claims priority under 35 U.S.C. § 119(a) to both British Patent Application No. 0320168.8, filed on 28 Aug. 2003 and International Application PCT/GB2004/003805, filed 27 Aug. 2004, which designated the U.S. and that International application was published under PCT Article 21(2) in English.

This invention relates to a sensing device, and in particular to a dual mode sensing device.

The oil industry is continuously involved in extracting and separating heterogeneous mixtures, either for further processing and/or purification. For example, when extracting crude oil from the ground, the oil itself generally needs to be extracted from a heterogeneous mixture. Such a mixture may comprise primarily crude oil, as well as water, gas and entrained particles. An oil separator vessel is a device used to separate such a mixture, and is illustrated in FIG. 1.

As illustrated in FIG. 1, an oil separator vessel may comprise parallel plates 1, a weir 2 and the like, and these are utilised to separate an extracted mixture into its constituent parts. It is desirable not to extract mixtures from the separator, but to ensure that separation is undertaken within the vessel.

In use, a heterogeneous mixture 3 of crude oil 4, water 5, gas 6 and solids 7 is taken into the vessel. The mixture develops into a foam 8 and emulsion 9. The parallel plates 1 are used to separate the mixture into its various phases, and the weir 2 is utilised to skim off the less dense oil 4 from the water 5. Solids 7 are allowed to leave the vessel from an outlet 10 below the parallel plates 1. Similarly, gas is extracted from the separator from an outlet 11, water from an outlet 12 and oil from an outlet 13.

In attempting to separate the mixture 3, capacitance measurements can be utilised for imaging the mixture 3 and the corresponding phase distributions during the separation process. Such information can be used to make the oil separator vessel more efficient in its separation of the mixture 3, usually by real-time control of the weir 2, plates 1 and the like (as disclosed in PCT application number PCT/GB98/02271, publication number WO99/06891). However, capacitance measurement alone is not sufficient to characterise poorly defined (also referred to as fuzzy) interfaces 14, for example emulsions (graded interface of oil and water) and foams (graded interface of oil and gas), under all conditions. Furthermore, capacitance sensors arranged in a column often become fouled with oil residue.

It is an aim of the present invention to obviate or mitigate at least one of the aforementioned disadvantages.

According to a first aspect of the present invention, there is provided a sensing device, comprising: a first element and a second element; each of said elements comprising: a first electrode; a second electrode; a piezoelectric layer between and connected to the first and second electrode, wherein the first electrode, second electrode and piezoelectric layer of each element form a pressure wave transducer, and wherein the first and second elements are oriented such that the second electrode of the first element faces the second electrode of the second element, and said elements are displaced from one another such that the second electrodes form the plates of a capacitor.

The inventors have realised that the utilisation of pressure wave transducers provides the necessary added measurement modality: a combined pressure wave and capacitance device (i.e. a dual mode device) provides the necessary means for identifying and characterising poorly defined interfaces utilising the minimum number of component parts.

The first aspect of the invention is advantageous in that a single device can generate and detect pressure waves utilising a piezoelectric effect, while also forming a capacitor.

Most preferably, at least one element comprises thick-film materials and preferably, at least one of the first and second electrodes of one of said elements comprises gold. Most preferably, at least one of said piezoelectric layers is a 0-3 composite.

At least one of said elements may further comprise a guard ring surrounding a periphery of at least one of said electrodes.

The sensing device may be coated with a protective layer for protection from a working environment.

The device may comprise a plurality of pairs of said elements. Most preferably, the plurality of pairs of elements are spaced apart along a longitudinal axis of the device, each element within a pair being disposed either side of said axis.

According to a second aspect of the present invention, there is provided a sensing method comprising: operating a sensing device as described above, the device being located with the elements of said device disposed either side of a region of interest; applying, via the first and second electrode of the first element, a first electric field across the piezoelectric layer of said first device such that the piezoelectric layer is made to expand or contract, thereby generating a pressure wave; detecting the pressure wave via the expansion or contraction of the piezoelectric layer of the second element and consequential generation of a second electric field in the first and second electrode of the second element; and measuring, via the second electrode of the first element and the second electrode of the second element, the capacitance of the region between the second electrodes.

The second aspect of the invention is advantageous in that a region of interest can be characterised utilising pressure waves and capacitance measurements by the provision of a single device. Pressure waves are generated by the piezoelectric layer expanding or contracting (i.e. it is mechanically deformed or undergoes a change in shape).

Most preferably, the capacitance measurement and pressure wave detection are used to characterise the region of interest, and most preferably, the generated pressure wave is ultrasonic.

Most preferably, the detection of the pressure wave and measurement of capacitance are undertaken in series.

According to a third aspect of the present invention, there is provided a sensing element comprising: a first electrode; a second electrode; a piezoelectric layer between and connected to the first and second electrode; wherein the first electrode, second electrode and piezoelectric layer of the element form a pressure wave transducer, and the second electrode forms a plate of a capacitor.

This element is the base unit of the sensing device, and is advantageous in that it can generate or detect pressure waves via the piezoelectric effect, and also forms the plate of a capacitor.

According to a fourth aspect of the present invention, there is provided a method of manufacture of an element, comprising: depositing a first layer, thereby forming a first electrode; depositing a piezoelectric layer; and depositing a third layer, thereby forming a second electrode, such that the first and third layers sandwich the piezoelectric layer.

Embodiments of the present invention will now be described with reference to the accompanying figures, in which.

Figure 2:
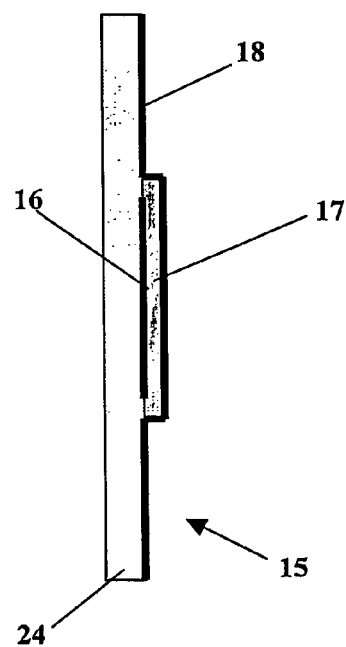
FIG. 2 illustrates a section view of an element in accordance with an embodiment of the invention.

FIG. 2 is a cross section view of an element 15 in accordance with an embodiment of the invention. An element 15 comprises a first electrode 16, a piezoelectric layer 17, a second electrode 18 and an insulation layer 24. In this embodiment, the insulation layer 24 acts as a substrate and a structural support for electrodes 16, 18 and piezoelectric layer 17. The first electrode 16, piezoelectric layer 17 and second electrode 18 form a pressure wave transducer. The second electrode 18 also forms a plate for a capacitor. A piezoelectric layer is a layer that generates electricity while under mechanical strain and, conversely, expands and contracts under the effect of an applied electric field. The insulation layer 24 is an electrical insulator. The insulation layer 24 can be ceramic, for example an alumina tile. The first electrode 16 is 15 µm thick and of surface dimensions 10 mm ×10 mm, these surface dimensions defining the overall size of the pressure wave transducer, but this does not restrict the size of the second, larger, electrode 18, which is also 15 µm thick but of surface dimensions 35 mm×35 mm. It should be noted that the Figures are not to scale, and are merely intended as illustrative aids. The first electrode 16 and second electrode 18 are substantially parallel and, together, sandwich the piezoelectric layer 17 which is 50 µm thick.

The first electrode 16, piezoelectric layer 17 and second electrode 18 are all deposited on substrate 24 in a known manner, for instance by screen printing a paste and then firing the paste to form a thick film layer. The first electrode 16 is deposited as a gold paste (ESL 8836 gold paste made by ElectroScience Laboratories, situated in Reading, England) and then fired to form a robust thick-film. The piezoelectric layer 17 is then deposited as a 0-3 composite, a lead zirconate titanate thick-film paste (PZT type 5A/glass paste, which is formulated at Southampton University, raw material provided by Morgan Electroceramic, situated in Southampton, England, to which the classification '5A' of the PZT material can be attributed), on top of the first electrode 16 (and in the example shown, extending beyond the electrode 16), and then fired. The term '0-3' refers to the fact that constituent binding material of the composite is unconnected along mutually orthogonal x, y and z axes, but that constituent piezoelectric material is active along all of these mutually orthogonal axes. The second electrode 18 is deposited as a gold paste (ESL 8836 gold paste) and then fired, thereby forming a thick film that sandwiches the piezoelectric layer 17 between the first electrode 16, insulation layer 24, and second electrode 18. Thick-films have been utilised as they are compact, robust, relatively inexpensive and are versatile enough to fabricate a combined pressure wave transducer and capacitor in a single device. Thick-films are particularly suited for employment in environments comprising high temperature fluids such as water.

Figure 3:
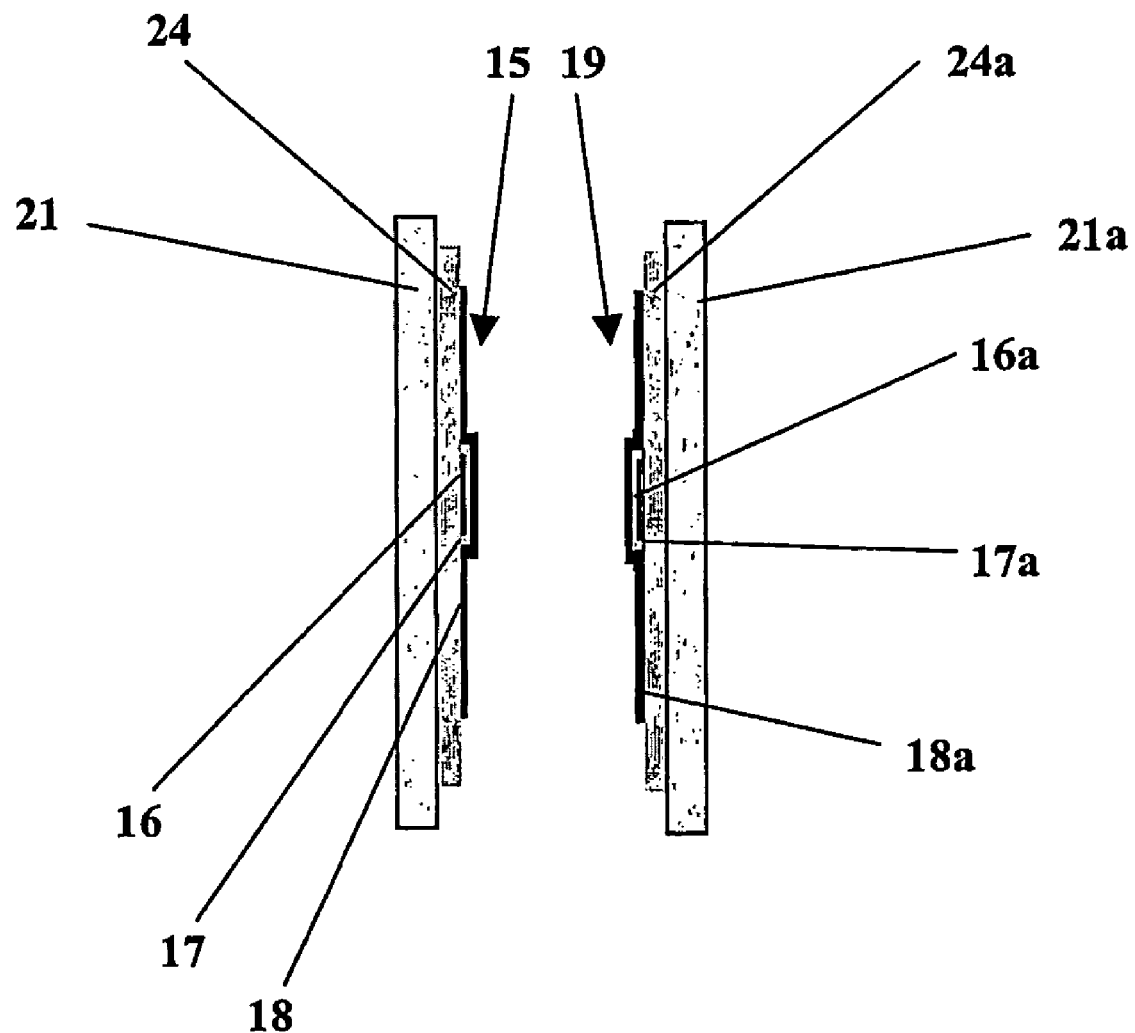
FIG. 3 illustrates a section view of a device in accordance with a first embodiment of the invention.

FIG. 3 illustrates a cross section view of a device in accordance with the first embodiment of the invention. The element 15 has been deposited in thick-film form on an alumina tile 24 in this case, and the alumina tile mounted to a steel support 21 to give the element substantial rigidity and support. The device comprises two of the elements as illustrated in FIG. 2, a first element 15 and a second element 19. The second element 19 is substantially the same as the first element 15, comprising a first electrode 16a, a piezoelectric layer 17a and a second electrode 18a. As with the first element 15 in this embodiment, the second element is deposited in thick-film form on an alumina tile 24a, which is mounted to a steel support 21a.

The mounted elements are oriented to face each other, the second electrode 18 of the first element 15 facing the second electrode 18a of the second element 19. The elements are displaced from each other by 20 mm. The second electrode 18 of the first element 15 is connected to the second electrode 18a of the second element 19, thereby forming a capacitor.

The elements may be coated in a protective layer, typically an epoxy layer (not shown) deposited on the external surface(s) of the elements. This gives some protection if the device is used in a physically harsh working environment, and a conveniently thin layer can be utilised such that the protective layer does not adversely affect the performance of the device. The protective layer may be deposited by any convenient means, such as brushing or scraping. Such a layer could, for example, be a 0.1 mm thick epoxy layer.

The device can be used to characterise a region of interest using pressure waves or capacitance measurements. Characterisation is achieved by locating the device so that such a region is in-between the two elements of the device.

Such a region of interest may be a fluid, or a heterogeneous mixture comprising a plurality of fluids and/or solid particulates. Characterisation of such a region of interest is achieved by using two complimentary measurements: a measurement of the transmission of ultrasound through, and the capacitance of, the region. By measuring the speed of ultrasonic waves through a region of interest, percentages of constituent materials can be extracted. Capacitance measurements are employed to identify properties in the dielectric constants of the region of interest. Changes in the overall capacitance, caused by changes in the dielectric constants, may correspond to an interface between phases in a heterogeneous mixture.

Each element has two electrical connections (not shown), one to the first electrode 16, 16a and one to the second electrode 18, 18a The electrical connections are further connected to electrical signal processing and electrical signal generating means. Electrical signal processing means are utilised for detection of signals at the electrodes for determination of capacitance between the elements, and/or detection of pressure waves incident on an element. Electrical signal generating means are utilised to supply appropriate electrical signals through the electrical connections to the electrodes 16, 16a, 18, 18a of one of the elements 15, 19 for generation of pressure waves. Using the first element 15 as an actuator of pressure waves, a varying electric field is applied across the piezoelectric layer 17 by the first 16 and second electrode 18. The electric field is of sufficient frequency to cause the piezoelectric layer 17 to expand and contract so as to generate pressure waves. Preferably the frequency is an ultrasonic frequency (i.e. a frequency exceeding 20,000 Hz), thereby generating pressure waves that are ultrasonic in nature. The second element 19 therefore acts as a sensor. Pressure waves impinging upon the second electrode 18a of the second element 19 cause it to move. Such movement causes the piezoelectric layer 17a of the second element 19 to expand and contract, thereby generating electrical energy. A varying electric field is thus established between the first 16a and second electrode 18a, allowing the detection of pressure waves. By measuring the electrical energy produced, the detected pressure waves may be characterised.

A capacitance measurement can be taken using a capacitor as formed by electrically connecting the second electrode 18 of the first element 15 and the second electrode 18a of the second element 19. Such a capacitance measurement can be taken in series or in parallel with a pressure wave measurement.

It will be obvious to one skilled in the art that the device has been described by way of example only, and that various modifications may be made to the device that would not extend beyond the protection afforded by the claims.

Figure 5A:
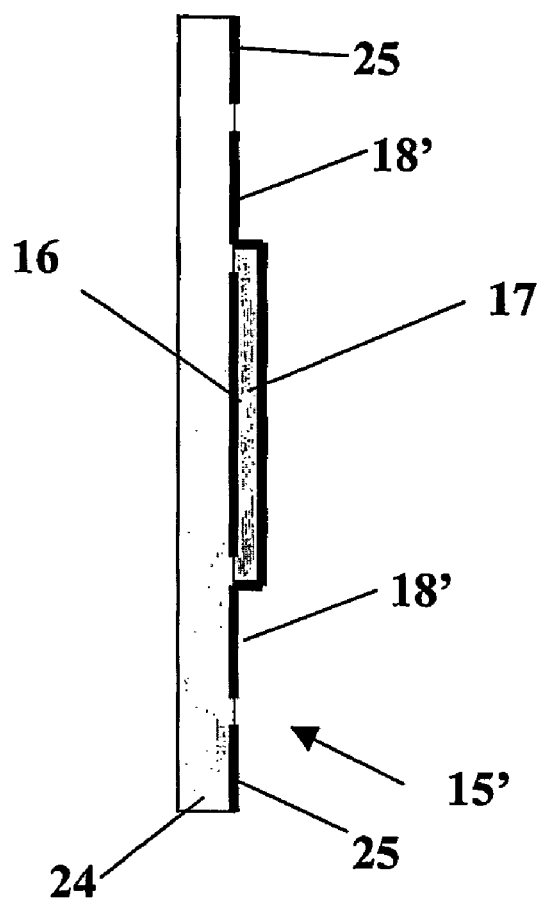
FIG. 5a illustrates a section view of an element in accordance with another embodiment of the invention.

For example, it will be appreciated that the element 15 illustrated in FIG. 2 can be modified in order to protect sensitive components from electrical damage. FIG. 5a is a section view, and FIG. 5b a plan view of an element 15' in accordance with another embodiment of the invention. The element 15' is similar to that described with reference to FIG. 2. Identical reference numerals are used to show similar features. However, in this embodiment, the second electrode 18' is smaller in surface dimension than that of FIG. 2. Further, a guard ring 25 is located around, but not in contact with, the periphery of the second electrode 18'. The guard ring 25 is deposited as a thick film conductor, such as a gold paste. In use, the guard ring 25 dissipates any capacitive pickup, thereby protecting the electrode that it surrounds from accumulating undesirable charge.

Figure 5B:
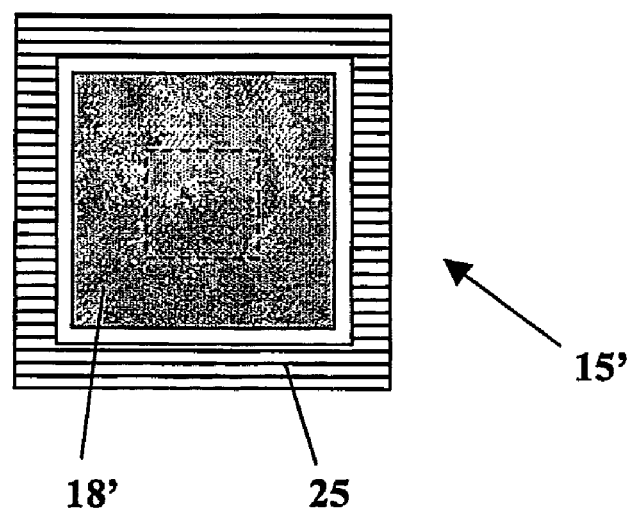
FIG. 5b illustrates a plan view of an element in accordance with another embodiment of the invention.

The devices have thus far been described with reference to the element 15 of FIG. 2, but it will be readily appreciated that the element 15' described with reference to FIGS. 5a and 5b may also be implemented in such devices.

Furthermore, it will be appreciated that the device may be of various dimensions. For example, the surface dimensions of respective layers may differ from those described above. The displacement of the two elements is only restricted by the ability of one element to detect the ultrasound generated by the other. The displacement is a function of the dimensions of the constituent layers of the elements, and also the properties of the region of interest (e.g. a fluid) to be characterised.

Also, it will be appreciated that as well as 0-3 composites, other piezoelectric materials may be employed as the piezoelectric layer of the elements constituting the device, such as, for example, a 1-3 composite or a 3-3 composite. Furthermore, it will be appreciated that the piezoelectric layer may be fabricated from other materials, not necessarily of a thick-film nature, such as sintered ceramic or polymer piezoelectrics. A device with the same functionality may be fabricated from thin-films. Thin-films may be deposited by chemical vapour deposition or sputtering techniques. Additionally, the electrodes may be fabricated from a metal other then gold, such as platinum or silver.

Furthermore, it will be appreciated that the insulation layer 24 in the above example is arranged so as to prevent electrical connection between two metal layers, namely the first and second electrode. It will be appreciated than in other configurations, a separate insulation layer is not necessary. For example, the piezoelectric layer may extend substantially beneath the second electrode, insulating it from the first electrode.

Figure 4:
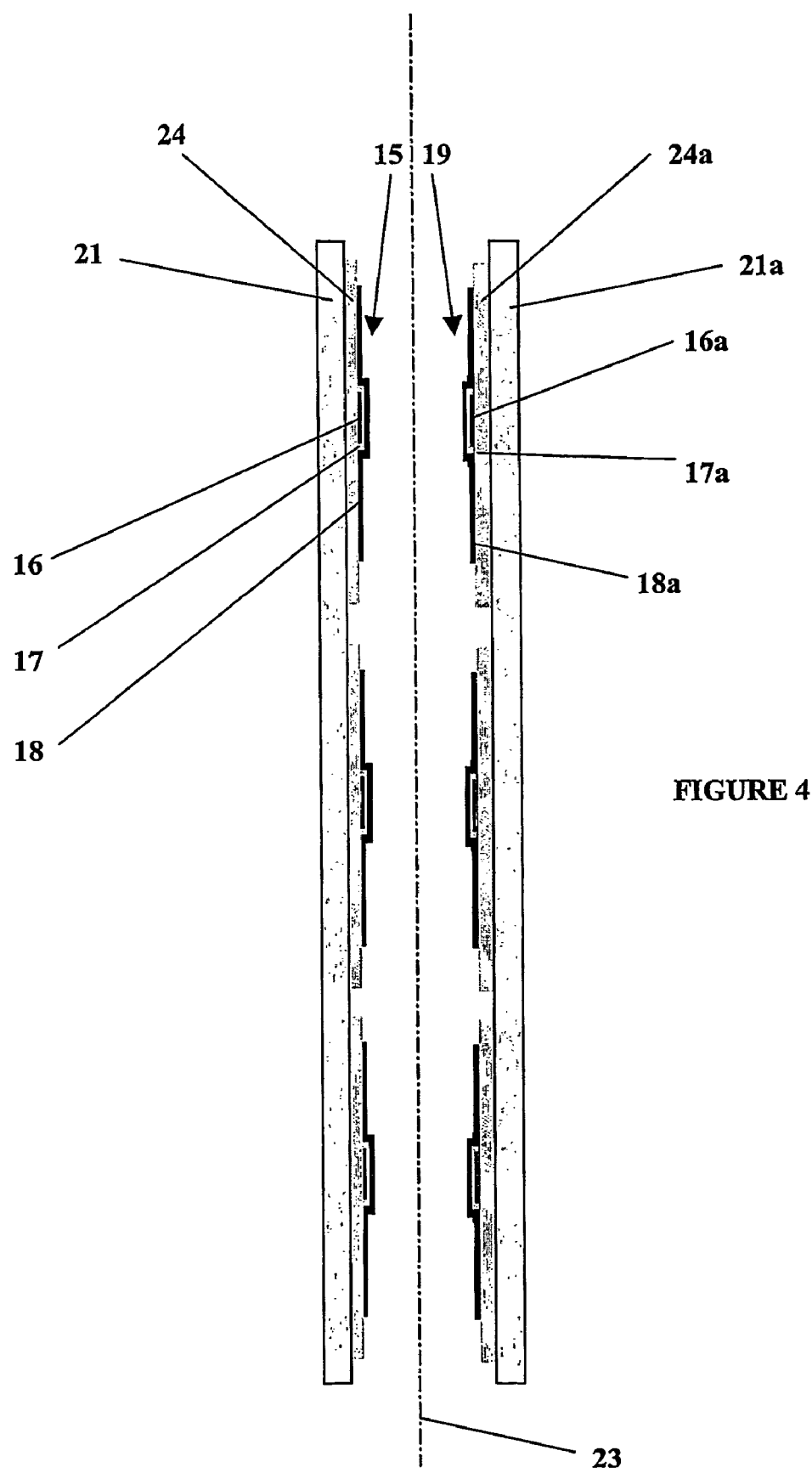
FIG. 4 illustrates a section view of a device in accordance with a second embodiment of the invention.

A further embodiment of the invention is illustrated in FIG. 4, whereby a plurality of devices as illustrated in FIG. 3 is provided in a longitudinal arrangement. The devices are arranged such that the steel supports 21, 21a of adjacent devices are parallel and in line with one another. In this embodiment, the steel supports 21, 21a form a continuous support. In this embodiment, the continuous support is shaped as a tube, with apertures within the surface of the tube such that material can still flow between the elements forming each device from outside the tube.

As illustrated, pairs of elements forming the devices are spaced apart along a longitudinal axis 23 of a device, each element within a pair being disposed either side of the axis.

Figure 1:
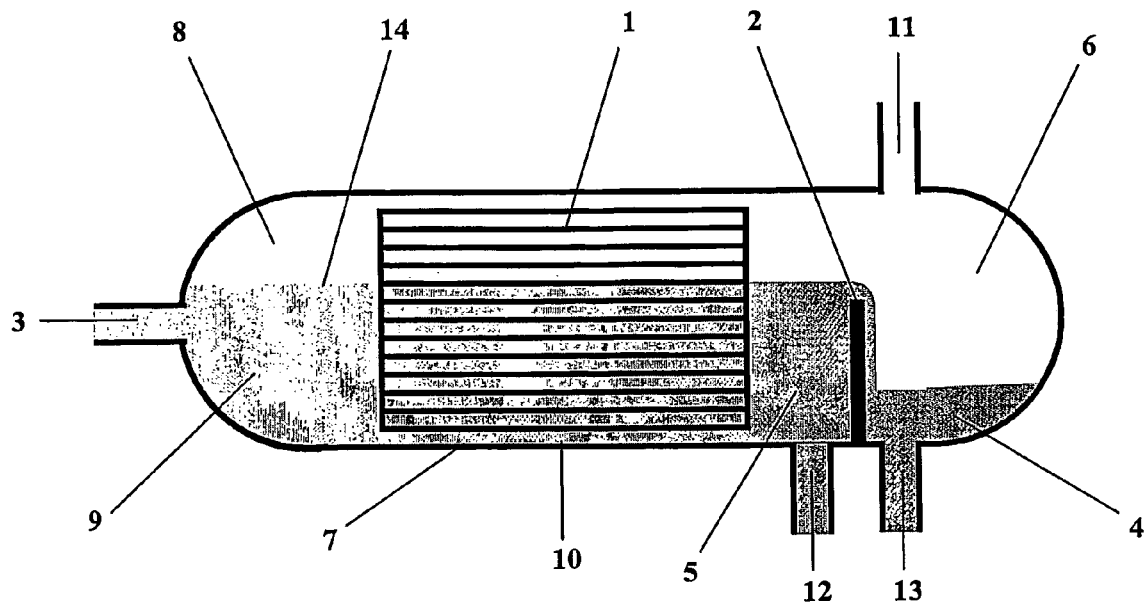
FIG. 1 illustrates a section view of a known oil separator vessel.

In use, multiples regions of interest can be characterised simultaneously. Hence, the plurality of devices can be positioned in the oil separator vessel of FIG. 1 and used to characterise multiple regions of interest and, furthermore, characterise and locate poorly defined interfaces between phases.

As well as the aforementioned material and dimensional variations of the device itself, it will be appreciated to one skilled in the art that the plurality of devices may be arranged in ways other than that exemplified above. The plurality of devices may form an array or matrix-like structure for example. Such a structure may take a number of forms.

For example, arranging a plurality of devices in a linear or longitudinal arrangement may form a simple one-dimension array of devices. A plurality of one-dimensional arrays may be arranged in a direction orthogonal to that of the linear arrangement, thus forming a two-dimensional array of devices. Repeating the two-dimensional array in a direction orthogonal to both the linear and two-dimensional repetition may form a three-dimensional array.

The invention claimed is:

1. A sensing method comprising:
    operating a sensing device, the sensing device comprising:
    a first element and a second element;
    each of said first element and the second element including:
        a first electrode;
        a second electrode;
        a piezoelectric layer between and connected to the first electrode and the second electrode;
    wherein the first electrode, the second electrode and the piezoelectric layer of each element form a pressure wave transducer, and wherein the first element and the second element are oriented such that the second electrode of the first element faces the second electrode of the second element, and said first element and said second element are displaced from one another to leave a space between the first element and the second element and such the second electrodes of said elements form the plates of the capacitor; and
    the device being located with the elements of said device disposed on opposite sides of a region of interest;
    the method further including:
    applying, via a first and second electrode of a first element, a first electric field across a piezoelectric layer of said element such that the piezoelectric layer is made to expand or contract, thereby generating a pressure wave;
    detecting the pressure wave via the expansion or contraction of the piezoelectric layer of a second element and consequential generation of a second electric field in a first and second electrode of the second element; and
    measuring, via the second electrode of the first element and the second electrode of the second element, capacitance of the region between the second electrodes.

2. A sensing method according to claim 1, wherein the capacitance measurement and pressure wave detection are used to characterise the region of interest.

3. A sensing method according to claim 1, wherein the generated pressure wave is ultrasonic.

4. A sensing method according to claim 1, wherein the detection of the pressure wave and measurement of capacitance are undertaken in series.

* * * * *